Figure 1:
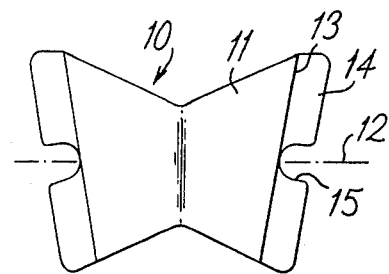

United States Patent [19]

Cavendish et al.

[11] 4,008,495
[45] Feb. 22, 1977

[54] PROSTHETIC BONE JOINT DEVICES

[75] Inventors: Michael Edward Cavendish, Rainford; Martin Arthur Elloy, Liverpool, both of England

[73] Assignee: National Research Development Corporation, London, England

[22] Filed: June 26, 1975

[21] Appl. No.: 590,823

[30] Foreign Application Priority Data

July 3, 1974 United Kingdom ............ 29483/74

[52] U.S. Cl. ................................. 3/1.91; 128/92 C
[51] Int. Cl.² ............................................ A61F 1/24
[58] Field of Search ........................... 3/1.9–1.913, 3/1; 128/92 C, 92 CA

[56] References Cited

UNITED STATES PATENTS

| | | | |
|---|---|---|---|
| 3,656,186 | 4/1972 | Dee | 3/1.91 |
| 3,839,742 | 10/1974 | Link | 3/1.91 |
| 3,852,831 | 12/1974 | Dee | 3/1 |

*Primary Examiner*—Ronald L. Frinks
*Attorney, Agent, or Firm*—Cushman, Darby & Cushman

[57] ABSTRACT

An endoprosthetic elbow joint device has a humeral component in the form of two like frusto-cones coaxially connected at their narrow ends and with their wider ends mutually convergently inclined to wedge into the intracondylar notch in the humerus when resected. This component is secured with cement, the component end faces being provided with a relieved structure of grooves or ribs extending in the relevant directions of inclination. The device also has an ulnar component of less than semi-circular toroidal form with its radially inner face complementary to and engaged with the above double cone. Again cement fixation is used in the ulna with a suitable relieved structure to key the component. Preferably this structure includes a chordally-directed groove to allow passage of a bone screw longitudinally through the olecranon so that the latter can be detached to expose the implantation site and thereafter reattached.

9 Claims, 10 Drawing Figures

U.S. Patent  Feb. 22, 1977  Sheet 2 of 2  4,008,495

PROSTHETIC BONE JOINT DEVICES

This invention concerns prosthetic bone joint devices and relates particularly to endoprosthetic elbow joint devices.

The forms of the latter devices in current usage normally involve a directly — linked mechanical hinge of all-metal construction which is secured to the humerus and ulna by way of intramedullary stems. While such hinged devices have proved satisfactory in the shorter term, it is now thought that they are subject to disadvantage in the longer term. More specifically, there is a tendency for the securement of the device to be weakened by transmission of stresses through the device itself. There is, in any case, disadvantage in the relatively large removal of bone and deep medullary penetration which is required for such hinged devices.

An object of the present invention is to reduce these disadvantages and, to this end, there is provided an endoprosthetic elbow joint device which comprises: a humeral component having a bearing surface defined by a surface of revolution about a longitudinal axis through said component, which surface is circumferentially convex but has a concave longitudinal shape converging in like manner from the opposite ends to the central region thereof, and having two fixation surfaces respectively located at said ends, which fixation surfaces are inclined in a like and mutually convergent manner in a transverse direction relative to said axis and are each formed with a relieved configuration: and an ulnar component having a bearing surface generally complementary with, but of lesser circumferential extent than, said humeral bearing surface for articulatory bearing engagement therewith, and having a fixation surface located remotely from said ulnar bearing surface and formed with a relieved configuration.

Normally said humeral bearing surface will be of a full 360° circumferential extent and will preferably have a relatively angular longitudinal shape substantially as provided by two like frusto-cones coaxially joined at their narrow end faces. Also, the ulnar bearing surface preferably has a longitudinal shape substantially complementary to said humeral bearing surface to afford lateral stability between these surfaces when engaged, as will be appreciated hereinafter.

The relieved configurations of the humeral fixation surfaces preferably comprise formations such as grooves and/or ribs extending in the respective directions of inclination. The corresponding configuration of the ulnar fixation surface preferably comprises similar formations extending both circumferentially and axially relative to the respective bearing surface axis. This configuration, in any case, preferably comprises a groove extending substantially perpendicularly to said axis to accommodate passage of an auxiliary fixation member therethrough.

For a fuller understanding of the invention and the intended manner of use thereof, the same will now be described by way of example with reference to the accompanying drawings in which:-

Figure 3:
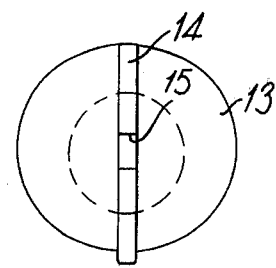
Figure 2:
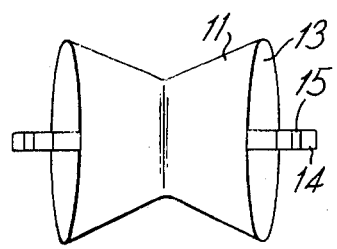
Figure 4:
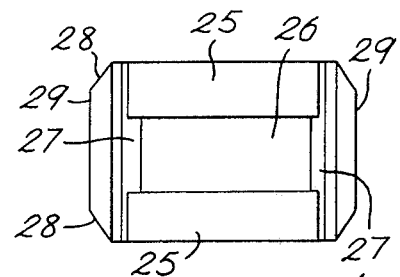
Figure 7:
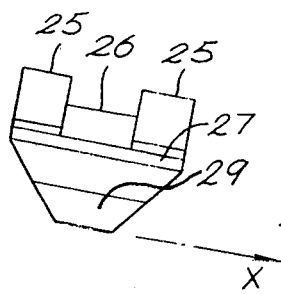
Figure 6:
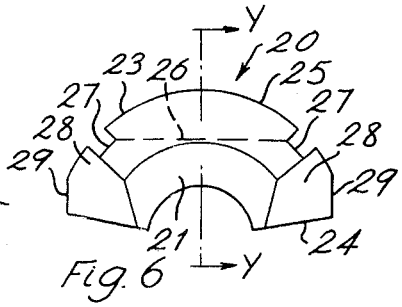
Figure 8:
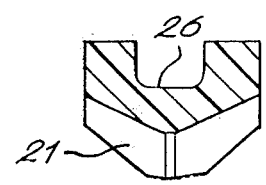
Figure 5:
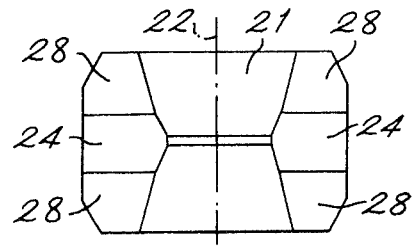
Figure 9:
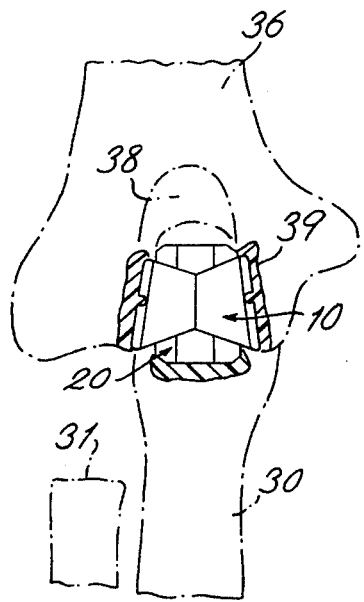
Figure 10:
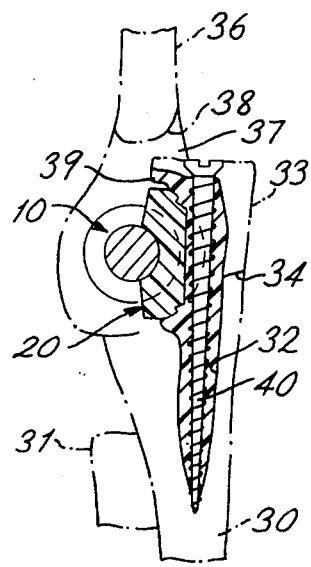

FIGS. 1, 2 and 3 respectively illustrate the humeral component of one embodiment of the invention in two mutually perpendicular side views and an end view, FIGS. 4 to 8 illustrate the ulnar component of said embodiment, respectively in opposed plan views, a side view, a view taken in the direction X, and a sectional view taken at Y—Y, FIG. 9 schematically illustrates the implanted locations of the embodiment components relative to the elbow joint bones in an anterior view, and FIG. 10 is a schematic lateral section of FIG. 9.

The illustrated humeral component is a solid body denoted generally at 10 and is of metal such as a suitable chrome - cobalt - molybdenum alloy or stainless steel. The body 10 is formed with a bearing surface 11 defined as a convex surface of revolution about an axis 12, but the longitudinal shaping of the surface 11 being concave by convergence in like manner from its ends towards its central region. More particularly this shape is angular and is substantially that formed by two like frusto-cones having their narrow end faces coaxially connected.

The end surfaces 13 of the body 10 serve as fixation surfaces, such surfaces being inclined in like and mutually convergent manner relative to a predetermined direction in the central radial plane of the body 10. The surfaces 13 are planar and converge at an inclusive angle of about 70°. The surfaces 13 are additionally formed with a relieved configuration by the provision of individual diametral ribs 14 extending in the respective directions of inclination, each rib having a notch 15 at its centre.

The illustrated ulnar component is also a solid body denoted generally at 20, but is of a suitable plastics material such as ultra high molecular weight polyethylene. The body 20 is formed with a bearing surface 21 defined as a concave surface of revolution about an axis 22, but with convex longitudinal shaping, the surface 21 being substantially complementary to that of the humeral bearing surface 11. However, unlike the latter surface which has a full 360° or circular circumferential extent over its major portion, the circumferential extent of surface 21 is less than 180° and preferably about 160°.

The remaining surfaces of the body 20 are seen to derive from its generally part-annular shaping defined by revolution about the axis 22. Thus the body has two like side surfaces 23 defined by transverse radial planes relative to axis 22, two like end surfaces 24 defined by longitudinal radial planes relative to axis 22, and a radially outermost part-cylindrical surface 25 centred on axis 22. This last surface serves as a fixation surface and is formed with a relieved configuration by the provision therein of a chordally-directed groove 26 which is symmetrically located in the body, and two axially-directed grooves 27 located adjacent respective ends of the groove 26. In addition, the ends of the body are tapered by the provision of chamfers 28 and 29 at each end of the side surfaces 23 and the outer surface 25, respectively.

In practice it will be appropriate normally to provide a metal X-ray marker in the ulnar component, but this is omitted from the drawings for reasons of clarity. However, such a marker preferably comprises two lengths of wire similarly located in grooves extending along the surface 25 on each side of groove 26, and with the wire ends located in bores in the grooves 27.

Similarly, it may be appropriate to provide bores or other formations in the components for co-operation with holding tools or jigs.

The intended manner of use of the illustrated components involves respective securement to the humerus and ulna with acrylic cement or other suitable gap-filling medium, the relieved configurations of the component fixation surfaces serving as a key for such medium.

A fuller understanding of the intended use will be gained from consideration of the following description of a preferred operative procedure in association with FIGS. 9 and 10 showing the components located, with their axes coincident and bearing surfaces in articulatory engagement in the humerus and ulna.

A mid-line incision is made posteriorly to expose the proximal end of the ulna (30) and the ulnar nerve is mobilized and moved to one side. The head of the radius (31) is excised and a hole (32) drilled axially through the olecranon (33) into the medullary canal of the ulna. The olecranon is divided transversely (34) and folded back on to the humerus (36) giving access to both the trochlea and the articular surfaces of the trochlea notch. The trochlea is excised by two saw cuts, inclined towards each other, and passing into the olecranon/coronoid fossae (37,38) thus making a slot to accommodate the humeral component of the prosthesis. Sufficient bone is removed from the area of the trochlear slot in both the ulna and olecranon to accommodate the ulnar component and a trial reduction made. A trial prosthesis is used for both these purposes. Some cancellous bone is gouged out of the sides of the slot to provide a key for the cement. The humeral component is then cemented into position, the tapered ends of the component driving cement (39) into the interstices of the cancellous bone. Cement in then pressed down the hole (32) in the ulna, into the prepared cavity for the ulnar component and into the keying slots of this component. The ulnar component is then located and the olecranon re-attached to the ulna by a bone screw (40) passing through the drilled hole into the ulnar medullary canal (32). The extension and flexion of the elbow are checked and pressure exerted on the olecranon to maintain reduction until the cement has hardened. The incision is then closed in layers without drainage. A tourniquet is used throughout.

The advantages of the proposed device as just exemplified include the possibility of affording a close approximation to the normal form of the humeral-ulnar joint, with an ability to subluxate or dislocate and so reduce the risk of fracture under abnormal loads. This approximation is furthered by employing a similar load bearing structure and so minimizing abnormal stress levels in the bones. Also, the device significantly reduces the necessary amount of bone removal compared to prior devices, so affording an increased salvage potential in the event of failure through causes such as post-operative infection, and the device is substantially enclosed in bone when implanted, so reducing the post-operative problems which can arise with subcutaneous implants. It is also to be noted from the illustrated example that the device can comprise symmetrical components suited to use in a left and right elbow.

Lastly, while the invention has been described with more particular reference to the illustrated example, it will be appreciated that the invention is capable of variation within the scope of the introductory discussion thereof hereinbefore.

We claim:

1. An endoprosthetic elbow joint device comprising: a humeral component having a bearing surface defined by a surface of revolution about a longitudinal axis through said component, which surface is circumferentially convex but has a concave longitudinal shape converging in like manner from the opposite ends of the central region thereof, and having two fixation surfaces respectively located at said ends, which fixation surfaces are inclined in a like and mutually convergent manner in a transverse direction relative to said axis, are each wholly bounded within a space defined by continued longitudinal projection of said bearing surface, and are each formed with a relieved configuration; and an ulnar component having a bearing surface generally complementary with, and in articulatory bearing engagement with, but of lesser circumferential extent than, said humeral bearing surface, and having a fixation surface located remotely from said ulnar bearing surface and formed with a relieved configuration.

2. A device according to claim 1 wherein the relieved configuration of each of said humeral fixation surfaces comprises an elongate structure extending in the direction of inclination of the relevant surface.

3. A device according to claim 2 wherein said structure is located in a diametral plane of said humeral bearing surface.

4. A device according to claim 3 wherein said structure comprises a rib which is notched in an intermediate longitudinal region thereof.

5. A device according to claim 1 wherein said humeral and ulnar bearing surfaces respectively extend circumferentially through 360° and an angle less than 180°.

6. A device according to claim 5 wherein said humeral bearing surface has a shape substantially defined by two like frusto-cones coaxially joined at their narrow end faces.

7. A device according to claim 5 wherein said ulnar component is substantially wholly defined by a surface of revolution and is convergently tapered at its circumferential end portions over such surface except for the respective bearing surface area thereof.

8. A device according to claim 1 wherein said relieved configuration of said ulnar component comprises a groove extending perpendicularly to the axis of the respective bearing surface.

9. A device according to claim 7 wherein said relieved configuration comprises a groove extending as a chord relative to the last-mentioned surface of revolution, and two elongate structures extending in the axial direction of such surface adjacent respective ones of said end portions.

* * * * *